United States Patent
Ma

(10) Patent No.: US 12,024,496 B2
(45) Date of Patent: Jul. 2, 2024

(54) CONVERSION OF 1,2,5,6-HEXANETETROL (HTO) TO TETRAHYDROFURAN DICARBOXYLIC ACID (THFDCA)

(71) Applicant: Archer Daniels Midland Company, Decatur, IL (US)

(72) Inventor: Chi-Cheng Ma, Champaign, IL (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 870 days.

(21) Appl. No.: 17/046,663

(22) PCT Filed: Mar. 28, 2019

(86) PCT No.: PCT/US2019/024493
§ 371 (c)(1),
(2) Date: Oct. 9, 2020

(87) PCT Pub. No.: WO2019/199468
PCT Pub. Date: Oct. 17, 2019

(65) Prior Publication Data
US 2021/0032215 A1    Feb. 4, 2021

Related U.S. Application Data

(60) Provisional application No. 62/657,277, filed on Apr. 13, 2018.

(51) Int. Cl.
*C07D 307/18* (2006.01)
*B01J 21/18* (2006.01)
*B01J 23/644* (2006.01)
*C07D 307/24* (2006.01)

(52) U.S. Cl.
CPC ............ *C07D 307/18* (2013.01); *B01J 21/18* (2013.01); *B01J 23/6447* (2013.01); *C07D 307/24* (2013.01)

(58) Field of Classification Search
CPC .. C07D 307/18; C07D 307/24; C07D 307/68; B01J 21/18; B01J 23/6447
See application file for complete search history.

(56) References Cited

FOREIGN PATENT DOCUMENTS

| WO | WO 2014-209595 | 12/2014 |
| WO | WO 2015-156803 | 10/2015 |
| WO | WO 2016-141148 | 9/2016 |

(Continued)

OTHER PUBLICATIONS

Boeckman, et al. "The Dess-Martin Periodinane: 1,1,1-Triacetoxy-1,1-Dihydro-1,2-Benziodoxol-3(1h)-One." Organic Syntheses, vol. 77, 2000, p. 141. (Year: 2000).*

(Continued)

*Primary Examiner* — Clinton A Brooks
*Assistant Examiner* — Kyle Nottingham
(74) *Attorney, Agent, or Firm* — Andrew F. Nilles

(57) ABSTRACT

Disclosed herein are methods for synthesizing useful intermediates and/or products from 1,2,5,6-hexanetetrol (HTO), which itself can be derived from a sugar. In an aspect, a process is provided for production of THFDCA from 1,2,5,6-hexanetetrol (HTO). The process comprises the steps of (a) ring closing to form a ring compound and (b) oxidizing using a catalyst comprising platinum and bismuth to form an acid mixture. Step (a) may be performed before or after step (b).

1 Claim, 2 Drawing Sheets

(56) References Cited

FOREIGN PATENT DOCUMENTS

| WO | WO 2017-061858 | 4/2017 | | |
|---|---|---|---|---|
| WO | WO-2018002291 A1 | * | 1/2018 | ........... C07D 307/68 |

OTHER PUBLICATIONS

Google Patents. WO-2018002291-A1 machine translation. 2023. (Year: 2023).*

Despevroux, et al. "The Use of Precious Metal Catalysts Supported on Activated Carbon in Oxidation Reactions for The Synthesis of Fine Chemicals, Especially for The Selective Oxidation of Glucose to Gluconic Acid." Studies in Surface Science and Catalysis, vol. 55, 1990, pp. 159-168. (Year: 1990).*

Tanaka, Kazuhiko, et al. "Separation of Carboxylic Acids on a Weakly Acidic Cation-Exchange Resin by Ion-Exclusion Chromatography." Journal of Chromatography A, vol. 850, No. 1, Jul. 1999, pp. 187-196. https://doi.org/10.1016/S0021-9673(99)00232-0. (Year: 1999).*

Asano, T. et al., "Selective hydrodeoxygenation of 2-furancarboxylic acid to valeric acid over molybdenum-oxide-modified platinum catalyst", ACS Sustainable Chemistry & Engineering, 2016, vol. 4, pp. 6253-6257.

* cited by examiner

CONVERSION OF 1,2,5,6-HEXANETETROL (HTO) TO TETRAHYDROFURAN DICARBOXYLIC ACID (THFDCA)

CROSS-REFERENCE TO RELATED APPLICATIONS

This application is a national stage entry of International Application No. PCT/US19/24493, filed Mar. 28, 2019, which itself claims priority to U.S. Provisional Patent Application No. 62/657,277, filed Apr. 13, 2018, the contents of each are incorporated herein by reference.

TECHNICAL FIELD

The present invention relates to conversion of 1,2,5,6-hexanetetrol (HTO) to tetrahydrofuran dicarboxylic acid (THFDCA).

BACKGROUND ART

Biomass contains carbohydrates or sugars that can be converted into value added products. Production of biomass-derived products for non-food uses is a growing industry. Bio-based fuels are an example of an application with growing interest. Another application of interest is the use of biomass as feedstock for synthesis of various industrial chemicals from renewable hydrocarbon sources.

In recent years, an increasing effort has been devoted to find ways to utilize biomass as feedstock for the production of organic chemicals because of its abundance, renewability, and worldwide distribution. When considering possible downstream chemical processing technologies, the conversion of sugars to value-added chemicals is very important.

Heterogeneous catalysts are widely used in liquid phase oxidation reactions. Oxidation of alcohols, aldehydes and carbohydrates has mainly focused on the use of supported Pd and Pt catalysts. The catalytic reactions occur under mild conditions in the range of about 20 to 80° C., and at atmospheric pressure. Dimitratos et al. reported the use of Pd and Pt catalysts for selective oxidation of alcohols to organic acids. Dimitratos et al, *Pd and Pt catalysts modified by alloying with Au in the selective oxidation of alcohols*, Catalysis Letters, vol. 244, pp. 115-121 (2006).

Other examples of use of Pd and Pt catalysts in liquid phase oxidation reactions are disclosed in Bronnimann et al. *Direct oxidation of L-sorbose to 2-keto-L-gluconic acid with molecular oxygen on platinum- and palladium based catalysts*, Catalysis, vol. 150, pp. 199-203 (1994); Garcia et al., *Chemoselective catalytic oxidation of glycerol with air on platinum metals*, Applied Catalysis A: General, vol. 127, pp. 165-176 (1995); and Hronec et al., *Competitive oxidation of alcohols in aqueous phase using Pd/C catalyst*, Molecular Catalysis, vol. 83, pp. 75-82 (1993).

Oxidation of cinnamyl alcohol to cinnamyl aldehyde over Pt and/or Pd catalysts has been reported. For example, Mallat et al., *Catalyst potential: a key for controlling alcohol oxidation in multiphase reactors*, Catalysis Today, vol. 24, pp. 143-150 (1995), reported the selective aerial oxidation of cinnamyl alcohol to cinnamaldehyde over Pt supported on alumina gave 88.5% selectivity to cinnamaldehyde.

Other examples of oxidation of cinnamyl alcohol to cinnamyl aldehyde over Pt and/or Pd catalysts are disclosed in Mallat et al., *Selective oxidation of cinnamyl alcohol to cinnamaldehyde with air over Bi—Pt/Alumina catalysts*," Catalysis, vol. 153, pp. 131-143 (1995); Grunwaldt et al., *In situ EXAFS study of Pd/Al2O3 during aerobic oxidation of cinnamyl alcohol in an organic solvent*, Catalysis, vol. 213, pp. 291-295 (2003); and Hardacre et al., *Use of a rotating disc reactor to investigate the heterogeneously catalysed oxidation of cinnamyl alcohol in toluene and ionic liquids*, Catalysis, vol. 232, pp. 355-365 (2005).

Direct oxidation of a primary alcohol without the presence of a functional as not been widely studied under mild conditions with oxygen.

U.S. Pat. No. 9,593,064 discloses methods for synthesizing an ester or a carboxylic acid from an organic alcohol. The patent discloses that to form an ester, an alcohol is reacted with methanol or ethanol, in the presence of oxygen gas and a catalyst comprising palladium and a co-catalyst comprising bismuth, tellurium, lead, cerium, titanium, zinc and/or niobium (most preferably at least bismuth and tellurium). The patent discloses that, alternatively, that catalyst can be used to generate an acid from that alcohol, when water is also added to the reaction mix.

U.S. Pat. No. 9,409,506 discloses a method for preparing 2,5-furandicarboxylic acid (FDCA) by oxidizing 5-hydroxymethylfurfural (HMF) in water in the presence of a weak base and a supported catalyst comprising platinum and bismuth, in which the Bi/Pt molar ratio in the catalyst is between 0.1 and 0.3, and preferably between 0.15 and 0.3.

U.S. Pat. No. 8,501,989 discloses processes for producing an adipic acid product comprising the step of hydrodeoxygenating a tetrahydrofuranic substrate, e.g., tetrahydrofuran-2,5-dicarboxylic acid (THFDCA) by reacting the same with hydrogen in the presence of a hydrodeoxygenation catalyst (i.e., catalyst suitable for the step of hydrodeoxygenation), an added source of halogen and a solvent, to convert at least a portion of the tetrahydrofuranic substrate to an adipic acid product. The patent discloses preparing THFDCA from FDCA, and that FDCA can be produced from 5-hydroxymethylfurfural (HMF) by selective oxidation. The patent further discloses that adipic acid can be converted to a wide variety of downstream chemical products or intermediates including adipate esters, polyesters, adiponitrile, hexamethylene diamine (HMDA), caprolactam, caprolactone, 1,6-hexanediol, aminocaproic acid, and polyamide such as nylons.

There remains a need in the art for alternative chemical synthesis strategies for producing useful intermediates and/or products, e.g., THFDCA (a diacid), 2,5-anhydro-3,4-dideoxy-hexanoic acid (the monoacid corresponding to THFDCA), and adipic acid, particularly strategies involving readily available or obtainable sugars and having the flexibility of synthesizing a number of different products with commercially attractive yields.

SUMMARY OF THE INVENTION

In each of its various embodiments, the present invention fulfills the need for more efficient production of useful intermediates and/or products from readily available or obtainable sugars. In an aspect, the present invention provides more efficient production of useful intermediates and/or products from 1,2,5,6-hexanetetrol (HTO), which itself can be derived from a sugar. In an aspect, a process is provided for production of THFDCA from 1,2,5,6-hexanetetrol (HTO). The process comprises the steps of (a) ring closing to form a ring compound and (b) oxidizing using a catalyst comprising platinum and bismuth to form an acid mixture. In an embodiment, the catalyst may comprise 5% Pt(Bi) by weight on carbon. Step (a) may be performed before or after step (b).

When step (a) is performed before step (b), then step (a) comprises contacting HTO with an acid for a time sufficient to form the ring compound, wherein the formed ring compound is tetrahydrofuran dimethanol (also known as 2,5 bis (dimethyl) tetrahydrofuran). In an embodiment, the acid may be selected from the group consisting of sulfuric acid, phosphonic acid, carbonic acid and a water tolerant non-Bronsted Lewis acid. Further, when step (a) is before step (b), then step (b) comprises oxidizing the tetrahydrofuran dimethanol formed in step (a) while the tetrahydrofuran dimethanol is in contact with the catalyst such that an acid mixture is formed comprising at least one of tetrahydrofuran-2,5-dicarboxylic acid (THFDCA) or 2,5-anhydro-3,4-dideoxy-hexanoic acid. In an aspect, when 2,5-anhydro-3,4-dideoxy-hexanoic acid is formed as part of the acid mixture, the process may further comprise i) recovering the 2,5-anhydro-3,4-dideoxy-hexanoic acid from the acid mixture, ii) recovering the 2,5-anhydro-3,4-dideoxy-hexanoic acid from the acid mixture and oxidizing the same while in contact with a catalyst comprising platinum and bismuth to form THFDCA, or iii) oxidizing the 2,5-anhydro-3,4-dideoxy-hexanoic acid in the acid mixture while in contact with the catalyst used in step b) to form additional THFDCA.

When step (b) is performed before step (a), then step (b) comprises oxidizing HTO while the HTO is in contact with the catalyst such that an acid mixture comprising 2,5-dihydroxyadipic acid and 2-hydroxyglutaric acid is formed, wherein more 2,5-dihydroxyadipic acid is formed than 2-hydroxyglutaric acid. Further, when step (b) is performed before step (a), then step (a) comprises contacting 2,5-dihydroxyadipic acid formed in step (a) with an acid other than 2,5-dihydroxyadipic acid for a time sufficient to form the ring compound, wherein the formed ring compound is THFDCA. In an embodiment, the acid other than 2,5-dihydroxyadipic acid may be selected from the group consisting of sulfuric acid, phosphonic acid, carbonic acid and a water tolerant non-Bronsted Lewis acid.

In an aspect, a process is provided for production of THFDCA and its corresponding monoacid, i.e., 2,5-anhydro-3,4-dideoxy-hexanoic acid. In an aspect, the process comprises oxidizing tetrahydrofuran dimethanol while the tetrahydrofuran dimethanol is in contact with a catalyst comprising Pt and Bi such that an acid mixture is formed comprising at least one of tetrahydrofuran-2,5-dicarboxylic acid (THFDCA) or its corresponding monoacid (2,5-anhydro-3,4-dideoxy-hexanoic acid).

In an aspect, a process is provided for production of THFDCA comprising oxidizing HTO while the HTO is in contact with a catalyst comprising Pt and Bi such that an acid mixture comprising 2,5-dihydroxyadipic acid and 2-hydroxyglutaric acid is formed, wherein more 2,5-dihydroxyadipic acid is formed than 2-hydroxyglutaric acid. In a further aspect, the process comprises contacting the 2,5-dihydroxyadipic acid formed in the oxidizing step with an acid selected from the group consisting of sulfuric acid, phosphonic acid, carbonic acid and a water tolerant non-Bronsted Lewis acid for a time sufficient to form the ring compound, wherein the formed ring compound is THFDCA.

These and other aspects, embodiments, and associated advantages will become apparent from the following description.

The figures are to be understood to present embodiments of the invention to aid in understanding of the principles and reaction chemistry involved, but not to limit the scope of the invention as defined in the appended claims. As would be apparent to one of skill in the art having knowledge of the present disclosure, synthesis methods according to various other embodiments of the invention will utilize particular reagents and reaction conditions determined, at least in part, according to specific objectives.

DETAILED DESCRIPTION OF EMBODIMENTS

In an embodiment, the present invention discloses processes using a catalyst comprising Pt and Bi in an oxidizing step to form an acid mixture, wherein the acid mixture comprises THFDCA or an acid from which THFDCA may be synthesized.

In an aspect, a process is provided for production of THFDCA and its corresponding monoacid, i.e., 2,5-anhydro-3,4-dideoxy-hexanoic acid. In an aspect, the process comprises converting 1,2,5,6-hexanetetrol (HTO) to tetrahydrofuran dimethanol. In an aspect, the process comprises placing the tetrahydrofuran dimethanol in contact with a catalyst comprising Pt and Bi. In an aspect, the process comprises oxidizing the tetrahydrofuran dimethanol while the tetrahydrofuran dimethanol is in contact with the catalyst such that an acid mixture is formed comprising at least one of tetrahydrofuran-2,5-dicarboxylic acid (THFDCA) or 2,5-anhydro-3,4-dideoxy-hexanoic acid. Monoacid (2,5-anhydro-3,4-dideoxy-hexanoic acid) in the acid mixture may be further oxidized using the Pt(Bi) catalyst to form the desired THFDCA product, optionally after being separated from any THFDCA originally formed in the acid mixture. In an embodiment, both acids are formed, wherein more THFDCA is selectively formed than its corresponding monoacid. In another embodiment, more 2,5-anhydro-3,4-dideoxy-hexanoic acid is formed than THFDCA.

In an aspect, a process is provided for production of THFDCA comprising oxidizing HTO while the HTO is in contact with a catalyst comprising Pt and Bi such that an acid intermediate mixture comprising 2,5-dihydroxyadipic acid and 2-hydroxyglutaric acid is formed, wherein more 2,5-dihydroxyadipic acid is formed than 2-hydroxyglutaric acid. In a further aspect, the process comprises contacting the 2,5-dihydroxyadipic acid formed in oxidizing step with an acid selected from the group consisting of sulfuric acid, phosphonic acid, carbonic acid and a water tolerant non-Bronsted Lewis acid for a time sufficient to form the ring compound, wherein the formed ring compound is THFDCA.

Figure 1:
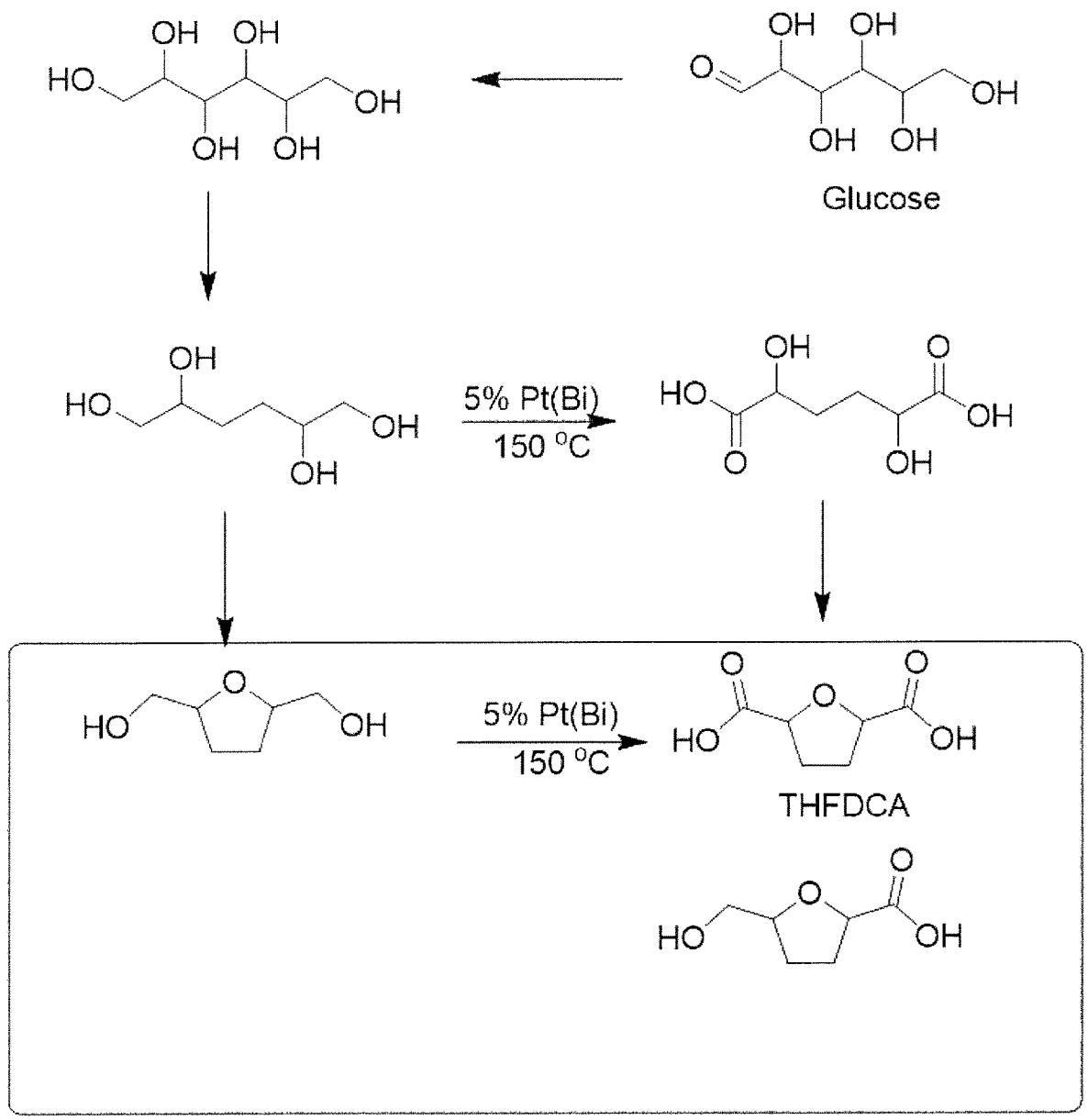
FIG. 1 shows synthesis of THFDCA and its monoacid, 2,5-anhydro-3,4-dideoxy-hexanoic acid, from glucose according to certain aspects of the invention.

FIG. 1 illustrates two pathways for producing THFDCA from a sugar. The pathways are common to each other in the aspect that they each may comprise four stages of operation, with the first two stages of operation being the same for each pathway. The pathways are also common to each other in the aspect that they both involve ring closing to form a ring compound, and oxidation of a compound while the compound is in contact with a catalyst comprising Pt and Bi, at an elevated temperature. The pathways differ in that in one pathway, the ring closing occurs first, followed by the oxidation step, whereas in the second pathway, oxidation is conducted first, followed by ring closing. The pathways are identified as Pathway 1 and Pathway 2 in the description that follows.

As shown in FIG. 1, in a first stage, a sugar, such as glucose, is hydrogenated so that it is converted to sorbitol.

The first stage may be carried out under neutral conditions, at a relatively low temperature, at relatively low pressure, and in the presence of a hydrogenation catalyst. The hydrogenation catalyst may contain copper and/or ruthenium. When the hydrogenation catalyst comprises copper, the solution comprising glucose should contains less than 2 ppm sulfide anion and less than 1 ppm chloride anions. Exemplary ruthenium catalysts are selected from the group consisting of ruthenium supported on carbon, ruthenium supported on a zeolite, ruthenium supported on $TiO_2$, and ruthenium supported on $Al_2O_3$. With the benefit of this disclosure, those skilled in the art will recognize that this first stage may be conducted in accordance with hydrogenation techniques disclosed in US 2017/0029393, at temperatures of 150 degrees Celsius and greater, especially from 160 to 220 degrees Celsius, and hydrogen pressures of 4.1 MPa and greater (600 psi and greater), especially 4.1 MPa (600 psi) to 6.9 MPa (1000 psi), for from 2 to 4 hours in a reaction vessel.

As shown in FIG. 1, in a second stage, sorbitol formed in the first stage may be converted to HTO. Those skilled in the art will recognize that, with the benefit of this disclosure, HTO may be produced from a C6 sugar alcohol, such as sorbitol (as shown in FIG. 1), and/or an R-glycoside in accordance with techniques disclosed in US 2017/0029393. For example, HTO may be synthesized from a starting compound that is C6 sugar alcohol and/or a C6 R-glycoside (wherein R is an alkyl moiety) present as at least 20% wt/wt in a solution comprising water by hydrogenation with hydrogen in the presence of a Raney copper catalyst, particularly by hydrogenation with the Raney copper catalyst deployed as a fixed bed in a reactor at temperatures of from 175 to 250 degrees Celsius and hydrogen pressures between 3.4 MPa to 17.2 MPa (500 to 2500 psi) at an average residence time of 2 hours in a continuous mode or between 1 and 4 hours in a batch mode. The sugar alcohols can be obtained from a commercial source or derived from any known method in the industry. In certain embodiments the sugar alcohols may be obtained by hydrogenation of C6 sugars or C6 R-glycosides. For example, sorbitol is typically obtained by hydrogenation of glucose over a Raney nickel catalyst. Ethyl glucoside may be obtained by hydrogenation of an acetyl cellulose pulp according to the methods described in US 2017/0029393. The R-glycoside can be obtained from a commercial source or derived from any known method in the industry. In certain embodiments the R-glycoside is an ethyl glucoside obtained from acylated cellulose pulp as described in US 2017/0029393. The reaction, however, can use any R-glycoside where the R group is a C1 to C4 alkyl group. Most preferably the R group is methyl or ethyl with the most commonly available glycosides being methyl glucoside or ethyl glucoside.

In Pathway 1, a third stage may be conducted under relatively mild conditions to convert HTO to a ring compound. In the third stage of Pathway 1, HTO may be contacted with an acid selected from the group consisting of sulfuric acid, phosphonic acid, carbonic acid and a water tolerant non-Bronsted Lewis acid (e.g., bismuth and scandium triflates or other triflates) for a time sufficient to form a ring compound, wherein the formed ring compound is tetrahydrofuran dimethanol (also known as 2,5 bis (dimethyl) tetrahydrofuran). With the benefit of this disclosure, those skilled in the art will recognize that this third stage of Pathway 1 may be conducted in accordance with HTO-to-2,5 bis (dimethyl) tetrahydrofuran (i.e., tetrahydrofuran dimethanol) conversion techniques disclosed in US 2017/0029393, using from 0.05% to 5% mol/mol of the starting materials of the acid catalyst, under reduced pressures ranging from 20 kPa (3.0 psi) to 40 kPa (6.0 psi) to facilitate continuous water removal and at temperatures from 120 to 150 degrees Celsius over from 1 to 4 hours.

In Pathway 1, the fourth stage may comprise oxidation of tetrahydrofuran dimethanol to a form an acid mixture of at least one of THFDCA or 2,5-anhydro-3,4-dideoxy-hexanoic acid, in the presence of a catalyst comprising Pt and Bi, e.g., 5% Pt(Bi) by weight on carbon. As shown in FIG. 1, the fourth stage of Pathway 1 may be carried out at an elevated temperature, e.g., 150° C. When oxidation of tetrahydrofuran dimethanol is carried out at such an elevated temperature, both acids are formed, wherein more THFDCA is formed than its corresponding monoacid 2,5-anhydro-3,4-dideoxy-hexanoic acid.

Figure 2:
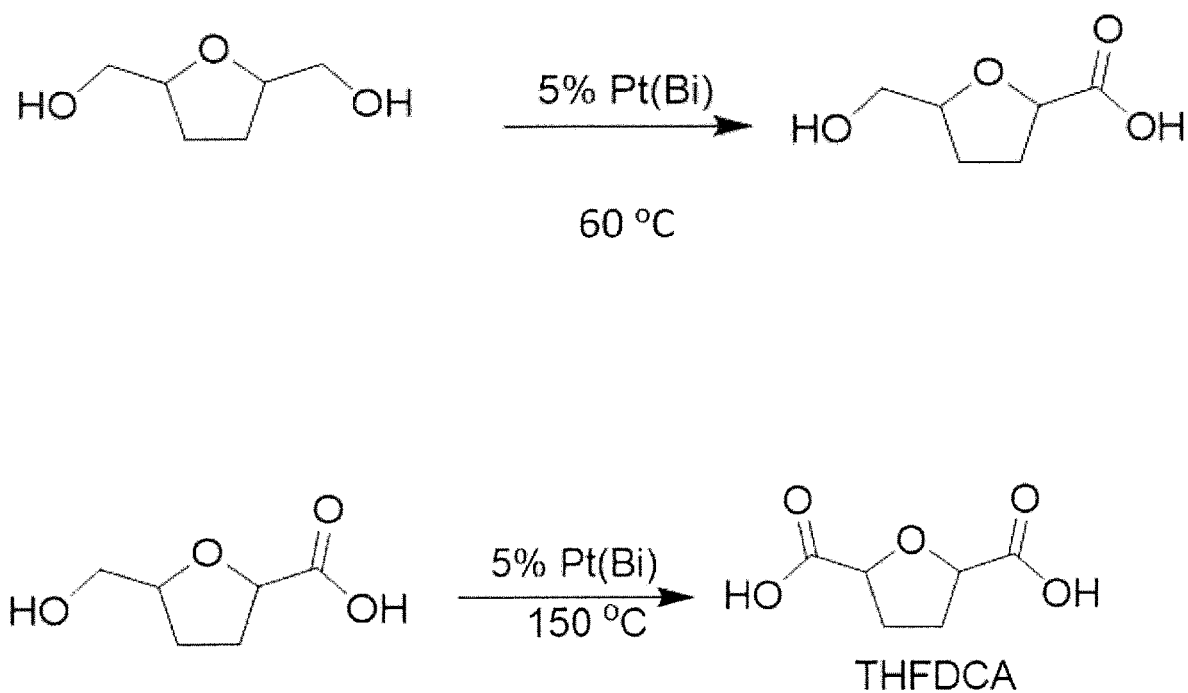
FIG. 2 shows synthesis of THFDCA from tetrahydrofuran dimethanol according to certain aspects of the invention.

An alternative embodiment of the fourth stage of Pathway 1 is shown in FIG. 2. In this alternative embodiment, oxidation of tetrahydrofuran dimethanol may be conducted at 60° C. and at atmospheric pressure in the presence of a catalyst comprising Pt and Bi, e.g., 5% Pt(Bi) by weight on carbon, to form the monoacid (2,5-anhydro-3,4-dideoxy-hexanoic acid), with no measurable yield of THFDCA. The benefit of the oxidation of tetrahydrofuran dimethanol to the monoacid under mild conditions is that it allows for easy control of reaction conditions. Further, the monoacid has potential for use in applications that differ from those considered for THFDCA. For example, the monoacid may be polymerized under conditions to form a polymer that is different from the polymer formed by the polymerization of THFDCA. Further, polymerization of THFDCA typically requires reaction with a dialcohol. Compare the following polymerization reactions of THFDCA versus polymerization of the monoacid:

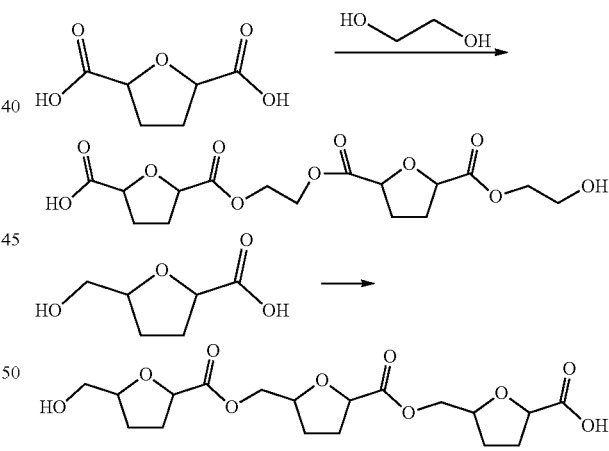

As shown in FIG. 2, when desired, of course, monoacid produced in the absence of measurable THFDCA may also be converted to the diacid THFDCA by oxidizing the monoacid at 150° C. in the presence of a catalyst comprising Pt and Bi, e.g., 5% Pt(Bi) by weight on carbon to form THFDCA. The time period for oxidation of the monoacid to the diacid can be shortened by conducting the oxidation at an elevated pressure greater than atmospheric pressure, for example, about 6.9 MPa (1000 psi) air.

As shown in FIG. 1, in Pathway 2, the third stage may comprise oxidation HTO to 2,5-dihydroxyadipic acid. In the third stage of Pathway 2, HTO is oxidized at an elevated temperature, e.g., about 150° C., at atmospheric pressure, in the presence of a catalyst comprising Pt and Bi, e.g., 5% Pt(Bi) by weight on carbon, to form 2,5-dihydroxyadipic acid.

In Pathway 2, the fourth stage may comprise contacting 2,5-dihydroxyadipic acid formed in stage 3 with an acid in an amount and manner for ring closing, thereby converting 2,5-dihydroxyadipic acid to THFDCA. This ring closing step may be performed by contacting 2,5-dihydroxyadipic acid with an acid selected from the group consisting of sulfuric acid, phosphonic acid, carbonic acid and a water tolerant non-Bronsted Lewis acid for a time sufficient to form THFDCA.

With the benefit of this disclosure, those skilled in the art will recognize that this fourth stage of Pathway 2 may be conducted in accordance with the same ring closing techniques disclosed in US 2017/0029393 and referenced above in connection with the third stage of Pathway 1.

The THFDCA formed in accordance with Pathway 1 or Pathway 2 may be separated from other compounds, e.g., the corresponding monoacid, i.e., 2,5-anhydro-3,4-dideoxyhexonic acid, that may be present. For example, this separation may be performed using ion-exclusion chromotography (IEC) and/or ion-exchange (IX), for example, by means of a polymethacrylate-based weakly acidic cation exchange resin using ion exclusion chromatography under acidic elution conditions, as described in Tanaka et al., "Separation of carboxylic acids on a weakly acidic cation-exchange resin by ion-exclusion chromatography", Journal of Chromatography A, vol. 850, no. 1, pp. 187-196 (August 1999) or by means of an anion exchange medium as taught by U.S. Pat. No. 9,487,465, "Process for the Separation of Mono- and Di-Carboxylic Acid Compounds".

With the benefit of this disclosure, those skilled in the art will recognize that THFDCA, produced using either Pathway 1 or Pathway 2, may be readily converted to adipic acid. For example, THFDCA may be converted to adipic acid by reacting the THFDCA with hydrogen, in the presence of a hydrodeoxygenation catalyst, a solvent and a source of halogen. The solvent may comprise a weak carboxylic acid. The term "weak carboxylic acid" as used herein means any unsubstituted or substituted carboxylic acid having a pKa of at least about 3.5, more preferably at least about 4.5 and, more particularly, is selected from among unsubstituted acids such as acetic acid, propionic acid or butyric acid, or mixtures thereof. Among the useful solvents, acetic acid is more preferred because it also is useful as a solvent in the subsequent hydrodeoxygenation of THFDCA. With the benefit of this disclosure, those skilled in the art will recognize that the conversion of THFDCA to adipic acid may be conducted in accordance with the THFDCA-to-adipic acid conversion techniques disclosed in U.S. Pat. No. 8,501,989, by reacting THFDCA with hydrogen in the presence of hydrogen iodide or hydrogen bromide and a solvent such as acetic acid, at temperatures from about 80 to about 200 degrees Celsius and especially from about 140 to about 180 degrees Celsius, with a partial pressure of hydrogen of from about 1379 kPa (200 psia) to about 13790 kPa (2000 psia), especially from about 2758 kPa (400 psia) to about 10343 kPa (1500 psia), in the presence of a solid phase hydrodeoxygenation catalyst comprising one or more d-block metals (Ru, Rh, Pd, Pt) which may be used alone, in combination with one or more rare earth metals (lanthanides) and with one or more main group metals (Al, Ga, Tl, In, Sn, Ph or Bi), on a support.

In an aspect, a process is provided comprising placing tetrahydrofuran dimethanol in contact with a catalyst comprising Pt and Bi. The process comprises oxidizing the tetrahydrofuran dimethanol while the tetrahydrofuran dimethanol is in contact with the catalyst such that an acid mixture comprising tetrahydrofuran-2,5-dicarboxylic acid (THFDCA) and corresponding monoacid (2,5-anhydro-3,4-dideoxy-hexanoic acid) is formed, wherein more THFDCA is selectively formed than the corresponding monoacid. In an embodiment, the oxidizing step is conducted at a temperature of about 145° C. to 155° C., and preferably about 148° C. to 152° C., and more preferably about 150° C. In an embodiment, the oxidizing step is conducted at a pressure of about 1000 psi air.

In an aspect, a process is provided comprising placing tetrahydrofuran dimethanol in contact with a catalyst comprising Pt and Bi. The process comprises oxidizing the tetrahydrofuran dimethanol while the tetrahydrofuran dimethanol is in contact with the catalyst at a first temperature and first pressure such that an acid mixture is formed comprising at least one of tetrahydrofuran-2,5-dicarboxylic acid (THFDCA) or its corresponding monoacid (2,5-anhydro-3,4-dideoxy-hexanoic acid), wherein more corresponding monoacid is selectively formed than THFDCA. In an embodiment, the first temperature may be about 55° C. to 65° C., and preferably about 58° C. to 62° C., and more preferably about 60° C. In an embodiment, the first pressure is at atmospheric pressure.

In an aspect, the process may further comprise placing the monoacid 2,5-anhydro-3,4-dideoxy-hexanoic acid in contact with a catalyst comprising Pt and Bi, and oxidizing the monoacid while the monoacid is in contact with the catalyst at a second temperature and second pressure such that a majority of the monoacid is converted to THFDCA. In an embodiment, the second temperature may be about 145° C. to 155° C., and preferably about 148° C. to 152° C., and more preferably about 150° C. In an embodiment, the second pressure about 1000 psi air.

In an aspect, a process is provided for production of THFDCA comprising oxidizing HTO while the HTO is in contact with a catalyst comprising Pt and Bi such that an acid intermediate mixture comprising 2,5-dihydroxyadipic acid and 2-hydroxyglutaric acid is formed, wherein more 2,5-dihydroxyadipic acid is formed than 2-hydroxyglutaric acid. In an embodiment, this oxidizing step is conducted at atmospheric pressure and a temperature of 145° C. to 155° C., and preferably about 148° C. to 152° C., and more preferably about 150° C. In a further aspect, the process comprises contacting the 2,5-dihydroxyadipic acid formed in the oxidizing step with an acid selected from the group consisting of sulfuric acid, phosphonic acid, carbonic acid and a water tolerant non-Bronsted Lewis acid for a time sufficient to form the ring compound, wherein the formed ring compound is THFDCA.

In an aspect, the present invention discloses oxidizing a primary alcohol with oxygen under mild conditions without the presence of a function group. In an aspect, a process and reaction system is disclosed wherein a sugar, such as glucose or dextrose, is ultimately converted to THFDCA, and THFDCA is converted to adipic acid. The reactor system may comprise four stages of operation, and each stage may be carried out in a separate reactor.

The following examples are set forth as representative of aspects of the present invention. These examples are not to be construed as limiting the scope of the invention as other equivalent embodiments will be apparent in view of the present disclosure and appended claims.

EXAMPLES

Example 1. Tetrahydrofuran dimethanol (35 g), 100 ml of de-ionized water and 2 g of the platinum-bismuth, were added to a 3-necked flask equipped with a condenser. The reaction mixture was refluxed and continuously stirred in an oil bath at 60° C. An aqueous solution of NaOH (21 g in 40 ml) was added drop wise, after finishing addition, the mixture was heated to 150° C. for overnight (about 16 hours). During the course of the reaction, samples were withdrawn from the reaction mixture at regular time intervals and then stored at ambient condition before NMR analysis. Based on NMR data, the conversion of tetrahydrofuran dimethanol is 70% with 50% yield of THFDCA.

Example 2. Tetrahydrofuran dimethanol (4 g: cis/trans), 30 ml of de-ionized water, 2 g of NaOH and 0.5 g of the Pt(Bi)/C, were added to a 100 cc reactor. The reaction mixture was heated up to 150° C. with 6.9 MPa (1000 psi) of air for 3 hours. Based on NMR data, the conversion of tetrahydrofuran dimethanol is above 98%, with 87% yield of THFDCA and 13% of the monoacid, 2,5-anhydro-3,4-dideoxyhexonic acid.

Example 3. Tetrahydrofuran dimethanol (35 g), 100 ml of de-ionized water and 2 g of the platinum-bismuth, were added to a 3-necked flask equipped with a condenser. The reaction mixture was refluxed and continuously stirred in an oil bath at 60° C. An aqueous solution of NaOH (21 g in 40 ml) was added drop wise, and after finishing addition, the mixture was heated to 60° C. for overnight (about 16 hours). During the course of the reaction, samples were withdrawn from the reaction mixture at regular time intervals and then stored at ambient condition before NMR analysis. Based on NMR data, the conversion of tetrahydrofuran dimethanol is 91% with 89% yield of 2,5-Anhydro-3,4-dideoxyhexonic acid, and no measurable yield of THFDCA. The reaction is shown as follows (as well as in the upper portion of FIG. 2):

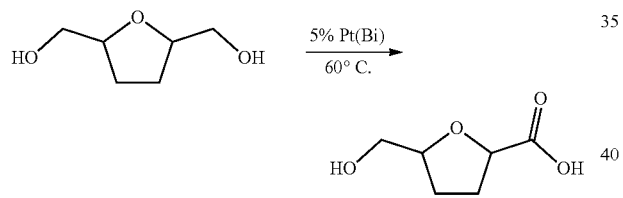

Example 4. 1,2,5,6-Hexanetetrol (HTO) 0.8 g, 0.8 g of the platinum-bismuth, and 1.0 g of NaOH in 20 ml of de-ionized water were added to a 3-necked flask equipped with a condenser. The reaction mixture was refluxed and continuously stirred in an oil bath at 60° C., the mixture was heated to 150° C. for overnight (about 16 hours). During the course of the reaction, samples were withdrawn from the reaction mixture at regular time intervals and then stored at ambient condition before NMR analysis. Based on NMR data, the conversion of HTO is 78% with 2,5-dihydroxyadipic acid as majority product and 2-hydroxyglutaric acid as a minor product. This reaction is the third stage of Pathway 2, previously described above. This reaction is shown as follows (as well as in FIG. 1):

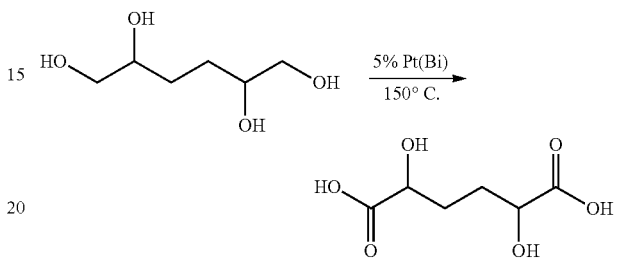

As can be seen from the above results, significant yields of THFDCA can be produced under the disclosed reaction conditions and with the described reaction mixture components. It is expected that process optimization, based on the teachings herein, can be conducted to increase yields of THFDCA, using HTO or tetrahydrofuran dimethanol according to the synthesis methods and overall teachings set forth in the present disclosure.

The invention claimed is:
1. A process comprising:
(a) oxidizing 1,2,5,6-hexanetetrol (HTO) while the HTO is in contact with a catalyst comprising Pt and Bi such that an acid mixture comprising 2,5-dihydroxyadipic acid and 2-hydroxyglutaric acid is formed, wherein more 2,5-dihydroxyadipic acid is formed than 2-hydroxyglutaric acid; and
(b) contacting 2,5-dihydroxyadipic acid formed in step (a) with an acid other than 2,5-dihydroxyadipic acid for a time sufficient to form the ring compound, wherein the formed ring compound is tetrahydrofuran dicarboxylic acid (THFDCA).

* * * * *